United States Patent [19]

Flynn et al.

[11] Patent Number: 4,588,160
[45] Date of Patent: May 13, 1986

[54] TUBE CLAMPING DEVICE

[75] Inventors: Daniel P. Flynn, St. Louis; Alan B. Ranford, Creve Coeur, both of Mo.

[73] Assignee: Sherwood Medical Company, St. Louis, Mo.

[21] Appl. No.: 716,307

[22] Filed: Mar. 27, 1985

[51] Int. Cl.4 .............................................. F16L 55/14
[52] U.S. Cl. ...................................... 251/10; 128/346
[58] Field of Search .................. 251/10, 4, 9; 128/346

[56] References Cited

U.S. PATENT DOCUMENTS

| Re. 31,584 | 5/1984 | Adelberg | 251/6 |
| 2,643,848 | 6/1953 | Hoffmann | 251/5 |
| 3,461,876 | 8/1969 | Miller, Jr. | 128/346 |
| 3,779,507 | 12/1973 | Clarke | 251/9 |
| 3,822,052 | 7/1974 | Lange | 251/10 |
| 3,847,370 | 11/1974 | Engelsher | 251/6 |
| 4,434,963 | 3/1984 | Russell | 251/7 |
| 4,439,179 | 3/1984 | Lueders et al. | 604/34 |
| 4,439,188 | 3/1984 | Dennehey et al. | 604/283 |

FOREIGN PATENT DOCUMENTS 646167 11/1950 United Kingdom .................. 135/47

OTHER PUBLICATIONS

Page 27 of "Medical Devices & Diagnostic Industry", vol. 6, No. 3, Mar. 1984.
Page 101 of "Infusion", vol. 7, May/Jun. 1983.
Thermoplastic Scientifics Inc., Advertisement for Dura-Clamp Flow Valves, 2/79.

Primary Examiner—Samuel Scott
Assistant Examiner—Allen J. Flanigan
Attorney, Agent, or Firm—Stanley N. Garber; Andrew J. Beck; William R. O'Meara

[57] ABSTRACT

A tube clamping device is provided which includes a pair of arms with tube clamping means thereon which are movable from an open position to a latched, closed clamping position in which the clamping means effects occlusion of a tube passing through the clamp. Each arm has a slot extending into the sidewall of the arm so that the tube can be laterally inserted and removed from the clamping device. A protective flexible sleeve provided with a slit for easy insertion onto the tube can be used to receive the clamping forces of the clamp to protect the tube.

5 Claims, 10 Drawing Figures

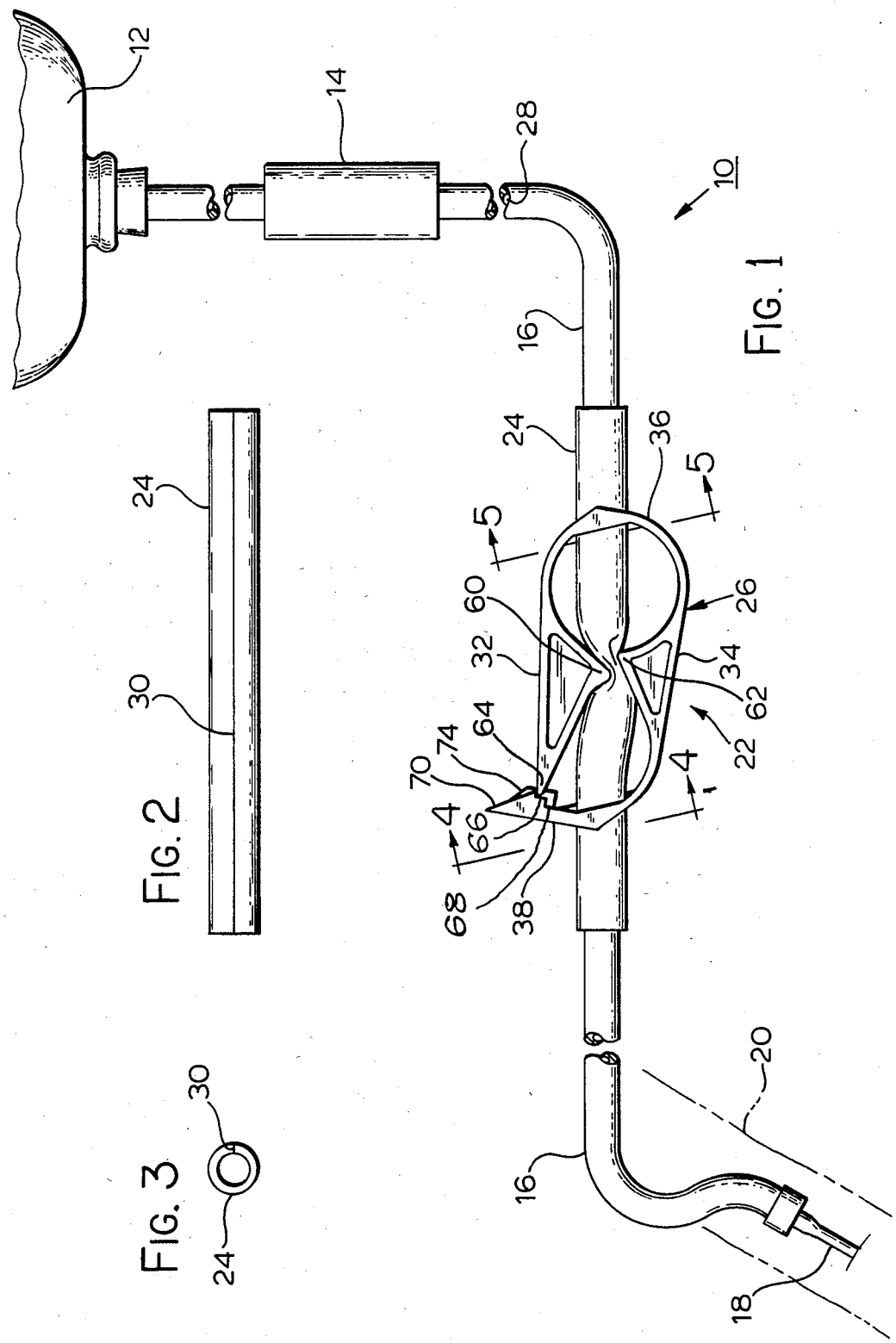

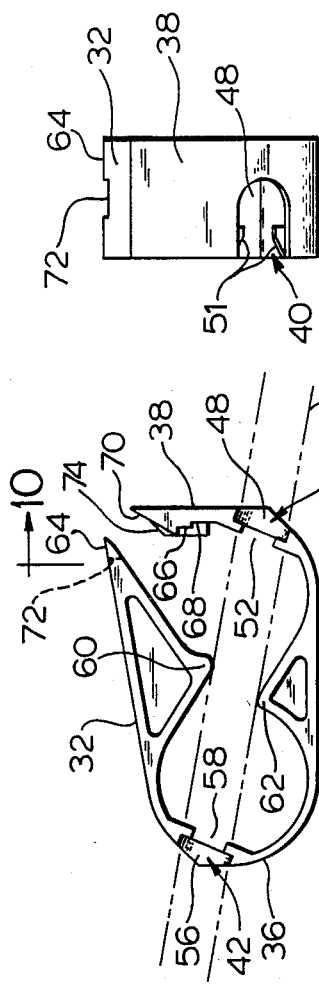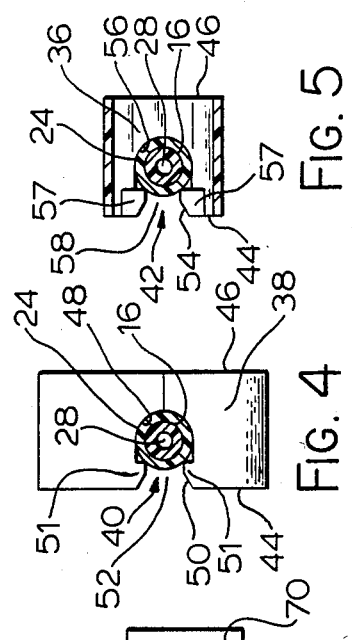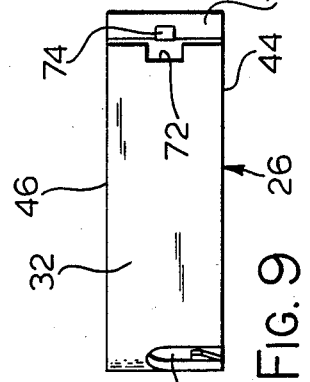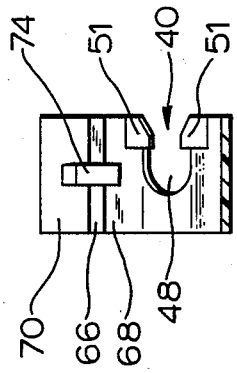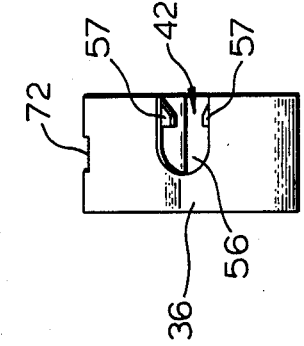

TUBE CLAMPING DEVICE

TECHNICAL FIELD

This invention relates to tube clamping devices and, more particularly, to a tube clamping device for selectively opening and closing resilient tubing.

BACKGROUND ART

Resilient tubing made from plastic or rubber is extensively used, for example, in the medical field for conveying fluids to and from patients. In the administration of intravenous liquids and in central veneous catheter applications, for example, it is often necessary or desirable to temporarily clamp the tube or catheter connected to a vein to close it for such purposes as disconnecting and reconnecting another source of intravenous liquid or for introducing medicaments into the tube. Tube clamping devices are, of course, used for many other medical applications.

Many types of tube clamping devices are well known, however, many such devices have certain undesirable features associated with them. In some cases, tube clamps were made such that the tube associated with it had to be inserted longitudinally or end first into holes in the tube clamping device. This meant that the clamp had to be applied prior to the insertion of the tubing into the patient or prior to the insertion of fittings or other devices to opposite ends of the tubing. Such clamping devices could not be installed after the tubing was connected in a fluid system and functioning to transfer fluid without interrupting the flow of the fluid in the system to disconnect a part of the system. Thus, such clamps were often applied during manufacture.

In many medical systems, especially where the tubing, such as a catheter, is maintained in operation over a relatively long period of time, such as hours or days, tube clamps may be repeatedly opened and closed a substantial number of times. Such repeated clamping operations have caused the tubing in some cases to become scuffed and result in a break in the sidewall of the tubing and fluid leakage. Tape has been applied around tubing with the clamp placed over the tape so as to prevent the tubing from breaking due to repeated clamping operations. Also, tube repair kits have been provided in order to repair tubing should an opening in the sidewall occur due to repeated clamping operations. Such tape and kits add to the cost of the apparatus, and additional time and work are required to prevent tube abrasion and the need to repair worn or leaking tubing. The danger of damaging the tubing walls and effecting a fluid leak while the tubing is connected with a patient is increased where the desired or required tubing is formed of a relatively soft material which is subject to wear, such as silicone rubber tubing or the like.

In order to avoid or reduce the chance of tubes or catheters wearing in areas as a result of repeated tube clamping operations, an outer protective tube or sleeve has been employed in some cases. The catheter or tube is threaded end first through the sleeve and the clamp before connectors or other elements are connected to the ends of the tube. Such protective sleeves cannot be applied to the tube after the tube is functioning to carry fluid unless the fluid flow is interrupted in order to install the sleeve on the tube. Also, it is difficult to clean the tubing sleeve and clamp for aseptic purposes because of the difficulty in removing the sleeve and clamp from the tube.

SUMMARY OF THE INVENTION

It is an object of the present invention to provide an improved tube clamping device which overcomes one or more of the above-mentioned problems.

A more specific object is to provide an improved tube clamping device which can be readily attached and removed from a tube even when the tube is in use.

Another object is to provide a tube clamping device which includes a tube clamp and a protective sleeve which can be readily attached and removed from a tube even when the tube is in use, and whereby the sleeve protects the tube against wear or breaking even if the tube clamp is repeatedly operated.

Still another object is to provide a flexible protective sleeve which protects against tube clamp damage and which is readily applied to the tube without inserting the tube end first into the protective sleeve.

In accordance with one aspect of the present invention, a tube clamping device is provided which includes a pair of resilient arms having complementary abutment means adapted to engage and clamp a tube disposed therebetween when the arms are in a tube clamping condition. The arms are connected together at one end and have cooperating latching means at the other ends to latch the arms in a tube clamping condition. The device has at least one slot extending inwardly from a side of the device whereby a tube can be laterally moved, sidewall first, into the slot with a portion of the tube disposed between the abutments.

In accordance with another aspect of the present invention, a tube clamping device is provided which includes a flexible protective sleeve having a slit extending from one end to the other to allow the sleeve to be placed around a tube, and a tube clamp adapted to engage and clamp the outer surface of the sleeve and close the tube when the clamp is in a tube clamping position.

In accordance with another aspect, a flexible protective sleeve is provided which has a slit from one end to the other so that it can be readily applied about a tube to protect the tube against wear due to the use of a tube clamp.

These, as well as other objects and advantages of the present invention, will become apparent from the following detailed description and accompanying drawings.

BRIEF DESCRIPTION OF THE DRAWINGS

FIG. 1 is a diagrammatical illustration of an intravenous infusion system utilizing a tube clamping device in accordance with a preferred embodiment of the present invention and with the clamping device in a closed condition;

FIG. 2 is a back side plan view of the protective sleeve of FIG. 1;

FIG. 3 is a left end view of the sleeve of FIG. 2;

FIG. 4 is a cross-sectional view taken along the line 4—4 of FIG. 1;

FIG. 5 is a cross-sectional view taken along the line 5—5 of FIG. 1;

FIG. 6 is a side elevational view of the tube clamp of FIG. 1 but with the clamp rotated to show the back side of it and with the clamp shown in an open condition;

FIG. 7 is a left end view of the clamp of FIG. 6;

FIG. 8 is a right end view of the clamp as shown in FIG. 6;

FIG. 9 is a top view of the clamp as shown in FIG. 6; and

FIG. 10 is a cross-sectional view taken along the line 10—10 of FIG. 6.

DESCRIPTION OF THE PREFERRED EMBODIMENT

Referring now to the drawings, and particularly to FIG. 1, a fluid administration or liquid infusion system 10 is shown for illustration including a source or bottle 12 of infusion liquid connected through a suitable conventional drip chamber 14 to a flexible tube 16. Tube 16 is shown connected to an intravenous catheter 18 disposed in the vein of a patient, a part of the patient being indicated in phantom at 20. Disposed on tube 16 is a tube clamping device indicated generally at 22 which is shown including a flexible and resilient protective tube or sleeve 24 surrounding a portion of the tube 16 in concentric relationship, and a tube clamp 26 disposed on the sleeve. Clamp 26 is shown in its tube clamping or closed condition in which the tube lumen, indicated at 28, is closed at the clamping device 22 so that liquid from source 12 cannot flow past the clamping device to the patient 20.

The tube 16 may be made of various materials which are resilient and collapsible when clamped or pinched. Tube 16 may, for example, be made of a natural or synthetic rubber, such as latex or silicone rubber, polyurethane or other suitable plastic or elastomeric material. Preferably, the tube 16 is made collapsible or flexible enough so that lumen 28 can be closed when clamped and resilient enough such that the lumen 28 will reopen when the clamping pressures are removed. The protective sleeve 24 is flexible and may be resilient, and may also be formed of various flexible plastic or elastomeric materials. In some cases, it may be made of the same material as tube 16. Sleeve 24 is preferably formed of a scuff and tear resistant material such as polyurethane material that is collapsible when clamped or pinched so as to allow the clamp 26 to occlude tube lumen 28 when the clamp is in its closed condition such as shown in FIG. 1. The sleeve 24 should be flexible enough and tube 16 resilient enough to allow the tube 16 to essentially return to its normally open condition, that is, with lumen 28 open when the clamp 16 is opened. The intravenous catheter 18 may also be formed of various plastic or elastomeric materials, such as polyurethane, silicone rubber, polyvinyl chloride, polyethelene or the like. Depending upon the materials used, the tubes 16, 18 and 24 may be made by the extrusion process or by other molding processes.

Clamp 26 is preferably formed of a relatively hard, somewhat flexible, resilient material and as a unitary or single piece member. Tube clamp 26 may be molded of a relatively rigid plastic or plastic composition such as one that includes polypropylene, acetal, polycarbonate, nylon or other suitable composition.

Sleeve 24, as also seen in FIGS. 2 and 3, has a slit 30 extending the entire length of the sleeve and which extends entirely through the sidewall of the sleeve. In this way, the sleeve 24 may be readily opened at the slit and pushed onto tube 16 without threading an end of the tube through the sleeve. Sleeve 24 can be quickly and easily placed on the tube 16 at any time such as during use of the system 10, that is, even after the patient and bottle 12 have been connected and fluid, such as an intravenous solution, is being delivered to the patient. The sleeve 24 is preferably of resilient plastic so that it may be readily inserted onto and off of tube 16 by spreading apart the abutting sidewalls of the sleeve at the slit 30 and laterally moving the sleeve onto the tube 16 with the sleeve returning to its normal cylindrical shape as seen in FIG. 3. The tube readily enters the sleeve sidewall first.

Clamp 26 includes a pair of resilient arms 32 and 34 integrally connected together at one end of the clamp, which end is indicated at 36. The opposite end of the clamp is indicated at 38. Each arm is generally relatively wide and relatively thin in cross-section and extends generally parallel with the tube 16 and sleeve 24. The clamp 26 is somewhat oval in shape when closed. The tube 16 and protective sleeve 24 pass through a pair of slots 40 and 42 disposed in the opposed ends 38 and 36 of the clamp, respectively, as seen in FIGS. 4 and 5.

The slots 40 and 42 are shown similar to each other. Slot 40 extends from one side 44 of the clamp 26 inwardly toward the opposed side 46 but is spaced from the opposed side. Slot 40 has a tube receiving slot portion 48 and an entranceway 50 at the side 44 which is shown to be tapered so the tube and sleeve can more easily enter the slot, sidewall first, from the side 44 and be forced or pushed by the fingers laterally inwardly, that is, in a direction generally normal to the longitudinal axes of the tube 16 and sleeve 24 and into the slot receiving portion 48. The slot 40 has a pair of facing protrusions 51 effecting a reduced slot portion 52 of smaller width than the maximum width or diameter of the tube receiving portion 48 and outer diameter of sleeve 24. Thus, the tube and sleeve must be urged and slightly compressed to move past the protrusions and through the reduced portion 52 when inserted into slot portion 48 as well as when removed from the tube clamp. In this way, the reduced or restricted portion 52 prevents the sleeve and tube from inadvertently moving out of the slot portion 48 but allows the tube to be readily manually moved into and out of the clamp when desired. Similarly, slot 42 at the opposite end 36 has an entranceway 54 at the side 44 of the clamp which connects with a tube receiving slot portion 56. Slot 42 has a pair of facing protrusions 57 forming a reduced or restricted slot portion 58 of smaller width than the maximum width or diameter of the sleeve to maintain the sleeve and tube in the slot portion 56 unless it is desired to manually remove the sleeve and tube from the slot 42. Preferably, the tube receiving portion 48 and 56 of the slots are sized so that they are only slightly larger than the outer diameter of the sleeve so that the sleeve and tube will remain in the tube receiving portions of the slots but will not restrict the tube lumen 28. Each of the slots 40 and 42 may be formed in various shapes and, while both are preferably open at the same side, such as side 44 of the clamp, the slots could have entranceways from different sides of the clamp. When both entranceways are on the same side as shown, it is generally somewhat easier to insert and remove the sleeve and tube from the clamp 26.

In FIGS. 6-10, the clamp is shown in its open condition without the sleeve and tube except that the sleeve 24 is shown in phantom in FIG. 6. Clamp arms 32 and 34 are also provided with a pair of integral complementary abutments 60 and 62, respectively, which are constructed so as to clamp or pinch the sleeve 24 and tube 16 between them when the clamp is closed as in FIG. 1 so as to occlude the lumen 28 of tube 16. The tube receiving slot portions 48 and 56 are in aligned relation with each other and the abutments 60 and 62 so that when a tube or tubes, such as tubes 16 and 24, are positioned in these slot portions, the tubes extend between the abutments 60 and 62. The abutments are shown generally triangular and disposed intermediate the opposed ends of the arms 32 ad 34 and extend toward each other. The abutments face each other and engage the sleeve 24, when employed, and bend and flatten portions of the tube clamped between them to occlude the tube lumen. The clamp 26 has a latching mechanism for latching the clamp closed which includes a tip 64 on arm 32 that is cooperable with a pair of notches 66 and 68 adjacent the end 38 of arm 34, as will be discussed hereafter.

The arms 32 and 34 are resiliently connected by the integral end portion 36 such that the arm 32 is normally biased away from the arm 34 in the open condition of the clamp as shown in FIG. 6, that is, the adjacent free ends of the arms are biased away from each other in the open condition of the clamp. In closing the clamp 26, the arm 32 is manually moved relative to arm 34 and against the bias force or resiliency of the arms until the tip 64 enters one or the other of notches 66 and 68 in the end 38 of the clamp. Major portions of the arms extend generally parallel to each other but end 38 which is an integral portion of the arm 34 extends generally normal to the parallel portion of the arm and is shown in FIGS. 1 and 6 extending generally vertically. End 38 is provided with an inclined upper end wall 70 so that the end 64 of arm 32 engages and slides downwardly on the inclined surface of wall 70 and into one of the notches to latch the arm 32 in a closed condition with the abutments 60 and 62 pinching the tube 16 and sleeve 24 to close lumen 28. In FIG. 1, the tip 64 is in notch 66. So that the clamp can be used with several different sizes of tubes and sleeves, the second notch 68 is formed just below notch 66 so that continued movement of the clamp arm 32 toward arm 34 will cause the tip 64 to leave notch 66 and enter notch 68 with the abutments 60 and 62 being moved closer to each other such that they can occlude a tube of smaller diameter than that of tube 16.

The arm 32 is dimensioned such that when it engages the inwardly inclined surface of wall 70, it urges the free or upper end of end portion 38 outwardly against the resilient force of the end portion and tends to apply a force against the end 64 to maintain the arm 32 in a latched position once it is in one of the notches 66 or 68. The upper wall of either notch and the resilient force of the end portion 38 of arm 34 securely hold the tip 64 of arm 32 in a latched condition. The upper wall of each notch extends generally longitudinally of the clamp and tube, and prevents upward movement of arm 32, as viewed in the drawings, when tip 64 is in a notch.

When it is desired to open the clamp 26 after it has been closed as in FIG. 1, the upper end of the end portion 38 of arm 34, such as surface 70, is moved away from the tip end or latch 64 of arm 32 to free the latch 64 from the notch and allow the resiliency of arm 32 to move the abutments 60 and 62 apart to thereby remove the clamping pressures from the tube 16 and sleeve 24 and open the lumen 28. With the clamp 26 open, the tube 16 and sleeve 24 can be readily transversly moved, sidewalls first, out of the slots 40 and 42 toward side 44 and out of the clamp. Also, if desired, the sleeve 24 can be readily removed from the tube 16 by laterally moving the tube 16, sidewall first through the slot 30 of the sleeve. Easy removal and replacement of the tube clamp 26 and sleeve 24 enable the clamp, sleeve and tube to be readily aseptically cleaned as well as allowing the clamping device 22 to be readily operated at different locations along the tube 16. Thus, lateral insertion, sidewall first, as opposed to threading a tube, end first, through a hole, greatly facilitates the use of the clamping device 22 in various manners.

The tip end 64 is provided with a central notch or groove 72 as best seen in FIG. 9 which, when the arm 32 is moved to a latching position, receives an integral alignment bar 74 as seen in FIGS. 1, 6, 9 and 10. Alignment bar 74 is adapted to engage either of the opposed sidewalls of groove 72 when the arm 32 is moved to close the clamp so as to prevent any excessive lateral movement of the arm 32 relative to the arm 34 during and after closure of the clamp 26. The opposed sidewalls of groove 72 and bar 74 cooperate to prevent excessive lateral movement between the arm 32 and 34 to ensure that the abutments 60 and 62 remain properly aligned with each other for controlled clamping of the sleeve and tube. Also, the alignment maintaining groove 72 and bar 74 reduce any tendency of the arms to twist and weaken their connection or hinge at the end 36 of the clamp 26 during relative movement of the arms during the closing and opening of the clamp. While the slot 42 reduces the effective width of the clamp end 36, which end provides a spring biasing effect or resiliency to arm 32, the alignment groove and bar prevent excessive strain on the end 36 during normal relative movement of the arms. The latching tip 64 of arm 32 extends laterally on both sides of alignment groove 72, and notches 66 and 68 extend laterally on both sides of alignment bar 74 to provide good latching and alignment for the arms 32 and 34.

It will be apparent that the tube clamp 26 may be used with various forms of tubing and in various applications. The clamp 26 can be used with tubing that includes a protective tube or sleeve or where only a tube, such as tube 16, is used, although in many applications a protective sleeve is desirable or necessary.

As various changes could be made in the above-described construction without departing from the true spirit and scope of the invention, it is intended that all matter contained in the above description and shown in the accompanying drawings be interpreted as illustrative.

What is claimed is:

1. A tube clamping device for collapsible resilient tubing comprising a pair of arms each having one end connected to one end of the other arm, means resiliently biasing the opposite ends of the arms apart, means for latching said opposite ends together against the force of said biasing means to close the clamp, a first slot adjacent one end of the device extending inwardly from a side thereof and adapted to receive a portion of the tubing sidewall first, a second slot adjacent the opposite end of the device extending inwarly from a side thereof for receiving another portion of the tubing sidewall first, a pair of abutment means respectively disposed on said arms for clamping the opposed sides of the tubing toward each other to occlude the lumen of the tubing when the tubing portions are in said slots and said opposite ends of said arms are latched together, and arm alignment maintaining means including means for limiting relative lateral movement between the said opposite ends of said arms when said opposite ends of the arms are latched, said alignment maintaining means including a groove on said opposite end of one of said arms and a bar on said opposite end of the other of said arms adapted to enter said groove when the clamping device is closed whereby the sidewalls of said groove limit relative lateral movement between said arms, said latching means including at least one notch on said other arm adjacent said opposite end thereof and an end portion of said one arm adapted to enter said notch, said groove being disposed in said end portion so that parts of said end portion are on opposite sides of said groove and are insertable into said notch, said notch extending on opposite sides of said bar.

2. A tube clamp comprising a body including first and second arms having free ends adjacent each other and having inner and outer sides, an end portion connecting said arms together and resiliently biasing said free ends apart, each of said arms having abutment means on the inner side thereof intermediate said end portion and the free end thereof for clamping tube means between said abutment means, said second arm having a first portion extending generally parallel with said first arm and an integral second portion extending generally normal to said first portion between said first portion and the free end thereof the inner side of said second portion facing said end portion, the second portion of said second arm having a notch disposed on the inner side thereof so that the free end of said first arm is movable into said notch for latching the free ends of said arms together, first and second cooperable arm alignment maintaining means respectively disposed on said arms for limiting movement of each of said arms in both lateral directions relative to the other of said arms when said arms are latched together, said first alignment means including laterally spaced walls on one of said arms adjacent the free end thereof, said second alignment means including a portion of the other of said arms adjacent the free end thereof movable into the space between said spaced walls for limiting said relative lateral movement, a first slot extending inwardly from a side edge of said body adjacent one end thereof to allow a portion of tube means to enter said first slot sidewall first, and a second slot spaced from said first slot extending inwardly from a side edge of said body to allow another portion of the tube means to enter said second slot sidewall first, said slots and said abutment means being located so that when the tube means portions are in said first and second slots the tube means extends between said abutment means.

3. The clamp of claim 2 wherein said first alignment means includes a groove extending inwardly from the free end of said one arm and said spaced walls are opposed sidewalls of said groove.

4. The clamp of claim 2 wherein said first and second alignment means are respectively integrally disposed on said first and second arms, respectively.

5. A tube clamp comprising a body of relatively rigid resilient plastic including first and second arms having free ends adjacent each other, a first end portion connecting said arms together and resiliently biasing said free ends apart, each of said arms having abutment means thereon intermediate said end portion and the free end thereof for clamping tube means therebetween, said second arm having a first portion extending generally parallel with said first arm and an integral second portion extending generally normal to said first portion thereof between said first portion and the free end thereof, the free end of said second arm having an inclined surface and a notch so that the free end of said first arm is slidably engageable with said inclined surface and movable into said notch for latching the free ends of said arms together, an alignment bar on said second arm adjacent the free end thereof, said first arm having a groove extending longitudinally inwardly from the free end for receiving said bar when the free ends of said arms are latched together, a first slot extending inwardly from a side edge of said first arm to allow a portion of tube means to enter said first slot sidewall first, and a second slot extending inwardly from a side edge of said second arm to allow another portion of the tube means to enter said second slot sidewall first, said slots and said abutment means being aligned so that when the tube means portions are in said first and second slots the tube means extends between said abutment means.

* * * * *

UNITED STATES PATENT OFFICE
CERTIFICATE OF CORRECTION

PATENT NO. : 4,588,160

DATED : May 13, 1986

INVENTOR(S) : David P. Flynn and Alan B. Ranford

It is certified that error appears in the above-identified patent and that said Letters Patent are hereby corrected as shown below:

On the front page, under References Cited, U. S. Patent Documents, the Buckman et al patent No. 3,942,228, issued March 9, 1976, Class 24/255SL, should be listed.

Signed and Sealed this

Nineteenth Day of August 1986

[SEAL]

Attest:

DONALD J. QUIGG

Attesting Officer

Commissioner of Patents and Trademarks